(12) United States Patent
Isaji et al.

(10) Patent No.: US 7,450,016 B2
(45) Date of Patent: Nov. 11, 2008

(54) DRIVER FATIGUE ASSESSMENT DEVICE AND METHOD

(75) Inventors: Kazuyoshi Isaji, Kariya (JP); Naohiko Tsuru, Handa (JP); Takahiro Wada, Takamatsu (JP); Hiroshi Kaneko, Okayama (JP)

(73) Assignees: Denso Corporation, Kariya (JP); National University Corporation Kagawa University, Takamatsu (JP)

( * ) Notice: Subject to any disclaimer, the term of this patent is extended or adjusted under 35 U.S.C. 154(b) by 180 days.

(21) Appl. No.: 11/295,759

(22) Filed: Dec. 7, 2005

(65) Prior Publication Data

US 2006/0132319 A1 Jun. 22, 2006

(30) Foreign Application Priority Data

Dec. 8, 2004 (JP) ............................. 2004-356026

(51) Int. Cl.
*G08B 23/00* (2006.01)
(52) U.S. Cl. ..................................... 340/573.7; 340/988
(58) Field of Classification Search ............ 340/573.74, 340/74, 457.576, 457, 576; 600/558; 351/209, 351/205, 210
See application file for complete search history.

(56) References Cited

U.S. PATENT DOCUMENTS 5,684,455 A * 11/1997 Williams et al. ............ 340/439
6,231,187 B1 * 5/2001 Munoz et al. ............... 351/209
2007/0132950 A1 * 6/2007 Victor et al. ................ 351/200

FOREIGN PATENT DOCUMENTS

| DE | 3803916 | 8/1989 |
|---|---|---|
| DE | 10135742 | 2/2003 |
| JP | 2002-025000 | 1/2002 |
| JP | 2003-080969 | 3/2003 |

OTHER PUBLICATIONS

English translation of Examination Report dated Apr. 19, 2007 for corresponding German Application No. 10 2005 058678.3.
Examination Report and English translation thereof for corresponding French Application No. 05 12487 dated Feb. 8, 2006.

* cited by examiner

*Primary Examiner*—George A Bugg
*Assistant Examiner*—Shirley Lu
(74) *Attorney, Agent, or Firm*—Harness, Dickey & Pierce, PLC

(57) ABSTRACT

A driver fatigue assessment device may include; a look information generator to generate look information regarding at least one of a driver's direction of a look and a locus at which a driver is looking; a visual stimulator to provide a visual stimulus within a driver's field of view at a first position and then move the location thereof to a second position; a change determination unit to determine whether the look information has changed in response to the movement of the visual stimulus; and a fatigue decision unit to assess driver fatigue based upon an output of the change determination unit.

18 Claims, 4 Drawing Sheets

DRIVER FATIGUE ASSESSMENT DEVICE AND METHOD

CROSS REFERENCE TO RELATED APPLICATION

This application is based on and incorporates herein by reference the entirety of Japanese Patent Application No. 2004-356026 filed on Dec. 8, 2004.

BACKGROUND

In recent years, driver's condition detecting devices have been proposed. For example, consider a first related technology (JP2003-80969A). The first related technology is concerned with the frequency at which a driver's direction of a look (or, in other words, viewing angle) changes. The driver's condition (or, in other words, quality) of alertness is determined based on the measured frequency.

As another example, consider a second related technology (JP2002-25000A). According to the second related technology, visual recognition time, reaction time, the number of times that visual recognition occurs, the number of times of look holding (i.e., that a look is held), etc. are detected as indicators of a driver's condition of alertness. The visual recognition time refers to the total time elapsed while a driver looked at a given subject, e.g., a spot on an information display screen. Reaction time refers to the time until the driver reacts to a visual stimulus. The number of times of visual recognition refers to the number of instances that a driver looked at a recurring visual stimulus. The number of times of look holding refers to the number of instances that an elapsed amount of time during which the driver gazed continuously at a persistent visual stimulus equaled or exceeded a threshold duration. The second related technology judges a driver's condition based on these detected parameters.

The first related technology mentioned above only detects a driver's direction of a look. Consequently, it is difficult to distinguish between a driver's intentional visual recognition and a coincidental look mistaken as a visual recognition. Coincidental looks can skew the assessment of the driver's condition, both positively and negatively.

The second related technology detects a driver's visual recognition of a visual stimulus whose position on the display screen is static. As such, it is difficult to assess, e.g., how well the driver can recognize an object that would jump into the driver's field of view.

SUMMARY

An embodiment according to the present invention provides a driver fatigue assessment device. Such a device may include: a look information generator to generate look information regarding at least one of a driver's direction of a look and a locus at which a driver is looking; a visual stimulator to provide a visual stimulus within a driver's field of view at a first position and then move the location thereof to a second position; a change determination unit to determine whether the look information has changed in response to the movement of the visual stimulus; and a fatigue decision unit to assess driver fatigue based upon an output of the change determination unit.

Figure 1:
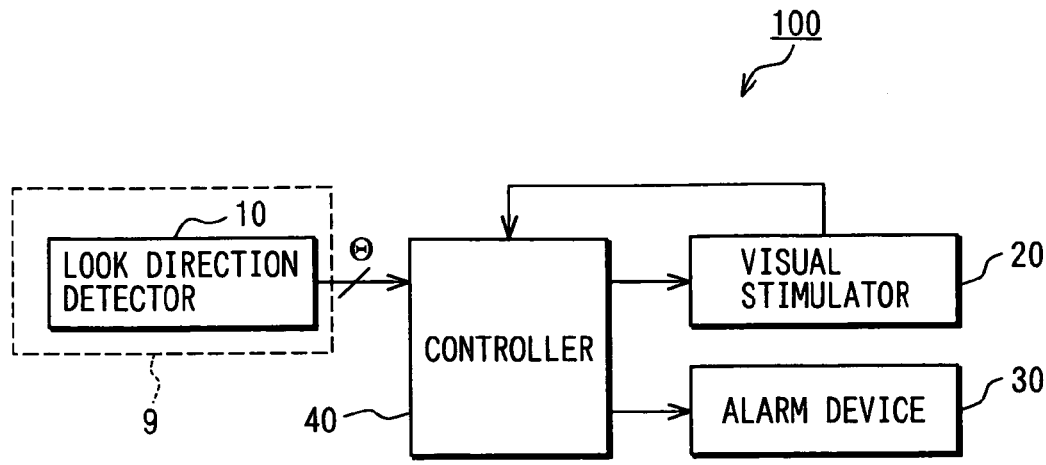
FIG. 1 is the block diagram of driver fatigue assessment device, according to an embodiment of the present invention.

The accompanying drawings are intended to depict example embodiments of the present invention and should not be interpreted to limit the scope thereof. The accompanying drawings are not to be considered as drawn to scale unless explicitly noted.

DETAILED DESCRIPTION OF THE EXAMPLE EMBODIMENTS

Now referring to the drawings, an explanation will be given of example embodiments of the present invention.

FIG. 1 is a block diagram of a driver fatigue assessment device 100, according to an embodiment of the present invention. The driver condition determining device 100 can be carried, e.g., in a vehicle, such as a car. The device 100 can include a look information generator 9 (that itself can include a look direction detector 10), a visual stimulator 20, an alarm device 30, and a controller 40.

The look direction detector 10 of the look information generator 9 is used in order to detect a driver's direction of a look, i.e., viewing angle. The look direction detector 10 is known, e.g., JP 2003-80969, the entirety of which is hereby incorporated by reference. In this look direction detector 10, an image-processing unit (not shown) calculates and outputs the direction of a look, namely $\Theta = \{\Theta_U, \Theta_V\}$, which (in two-dimensional surface-of-projection coordinates) includes a horizontal angle $\Theta_U$ and perpendicular angle $\Theta_V$. A look locus determination unit 12 (included within look information generator 9, see FIG. 2) calculates and outputs data P(X, Y) representing the coordinates at which the driver is looking in reference plane based upon this direction of a look data $\Theta = \{\Theta_U, \Theta_V\}$.

The visual stimulator 20 provides a visual stimulus to the driver, i.e., inserts the visual stimulus into the driver's field of view. For example, the visual stimulus can be located within a peripheral vision region of the driver's field of view. This visual stimulator 20 is responsive to control signals (e.g., start/stop, position of the visual stimulus, etc.) from the controller 40.

For example, the visual stimulator 20 can be a type of rear view mirror that includes a plurality of lights, e.g., LEDs, arrayed around a periphery of the rear view mirror. The visual stimulus can be presented to the driver by energizing, e.g., one of the plurality of LEDs on a rear view mirror 50 shown in FIG. 4, where such energization is depicted in FIG. 5. The position of the visual stimulus can be moved by energizing a different one (or more) of the lights. Other implementations of the visual stimulator 20 also can be suitable.

Figure 4:
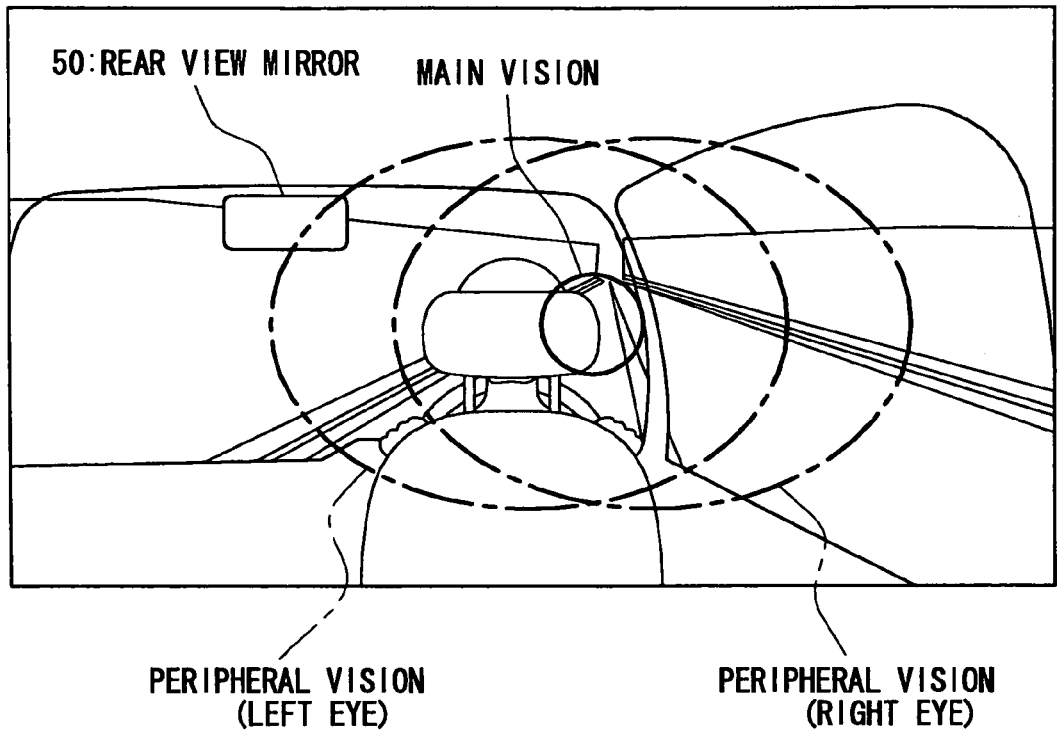
FIG. 4 is a figure, according to an embodiment of the present invention, for explaining the spatial relationship of a driver's main vision and a peripheral vision.
Figure 5:
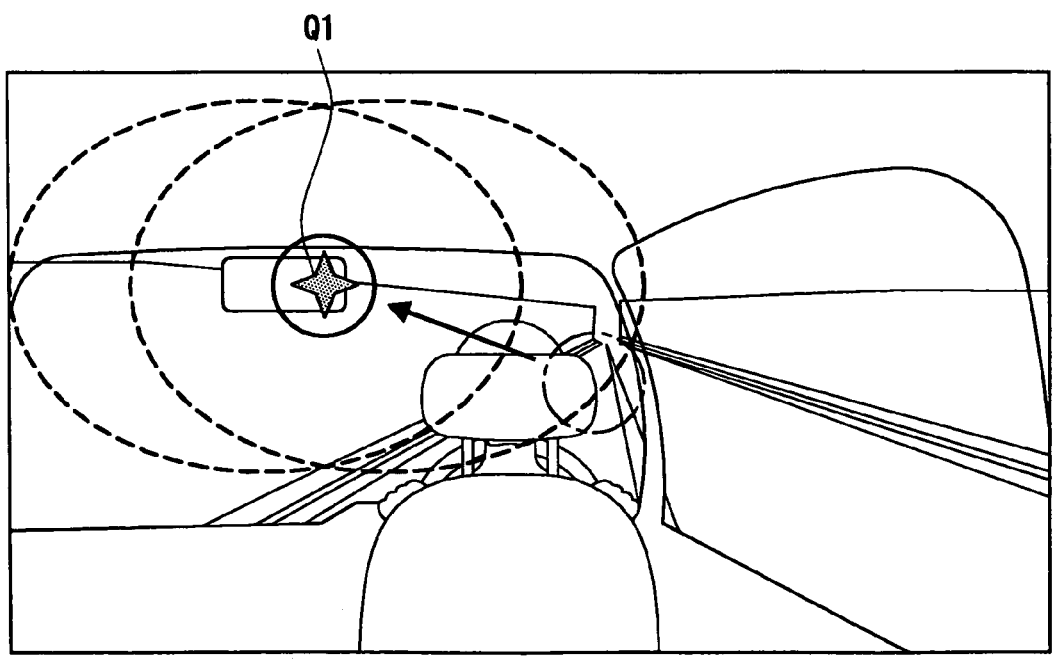
FIG. 5 is the figure showing an initial position of a visual stimulus provided with a driver's field of view, according to an embodiment of the present invention.

In FIG. 4, the driver's main viewing region (within the driver's field of view) is depicted. Also depicted in FIG. 4 are the peripheral-vision regions for the driver's left eye and right eye.

If the control device 40 concludes that the driver is fatigued, then the control device 40 can control alarm device 30 to generate an alarm to the driver, e.g., for the purpose of rousing the driver to a greater degree of alertness. The alarm can be visual and/or audible. For example, a visual alarm can be a brief, dazzling energization of multiple LEDs on the rear view mirror (in which case the alarm device 30 and the visual stimulator 30 overlap), or briefly energizing the dome light (not depicted) and/or map light (not depicted) multiple times, etc.

The controller 40 can be, e.g., a microcomputer. A controller 40 provides a input-and-output interface (I/O) which connects ROM, RAM, CPUs, etc. (none of which are illustrated).

Driver fatigue assessment can be triggered for a variety of reasons, for example, because an amount of time $t_{DRIVE}$ during which the driver has had to be alert equals a threshold amount of time $T_{FATIGUE}$ associated with the onset of fatigue. For example, $t_{DRIVE}$ can be the amount of time that the driver has been driving, that the driver has been sitting in the driver's seat, etc. In other words, if it is determined that elapsed alertness time, $t_{DRIVE}$, has met or exceeded a threshold $T_{FATIGUE}$, then this can be a reason to begin driver fatigue assessment. When controller 40 has determined that driver fatigue assessment should begin, then the controller 40 starts inputting look direction data θ and/or look position data P(X, Y) from the look direction detector 10.

Figure 2:
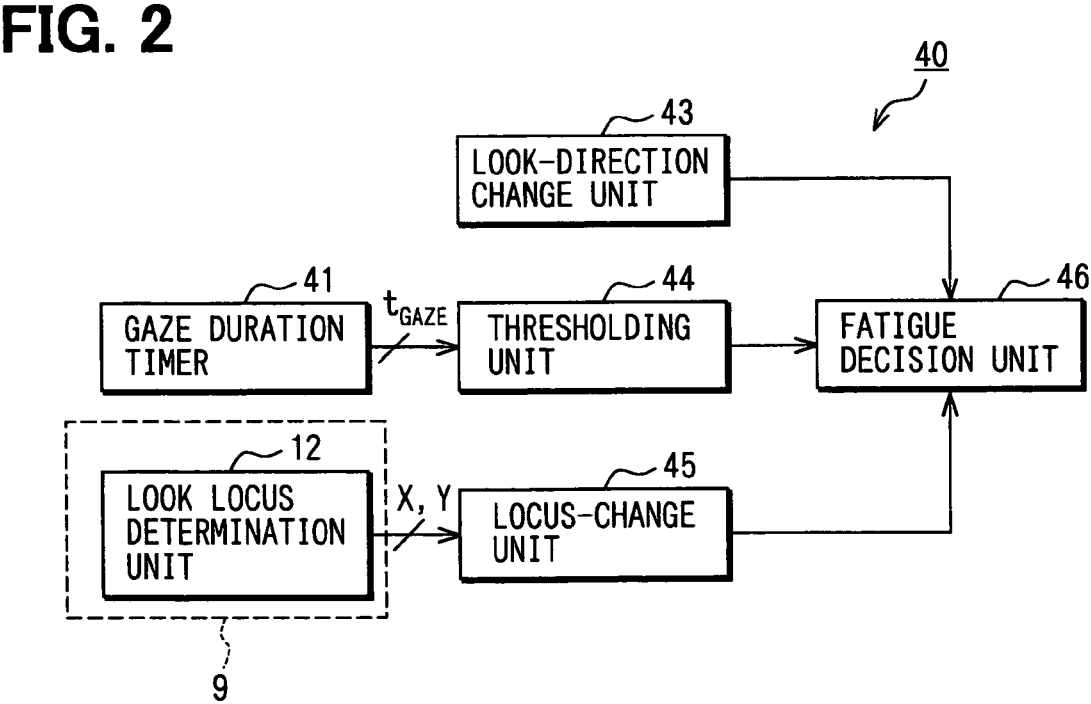
FIG. 2 is a functional block diagram of the controller of FIG. 1, according to an embodiment of the present invention.

FIG. 2 is a functional block diagram of a controller 40, according to an embodiment of the present invention. The controller 40 can include a gaze duration timer 41, a look-direction change unit 43, a thresholding unit 44, a locus-change unit 45, and a fatigue decision unit 46.

Based upon when look position data P(X, Y) is outputted from the look direction detector 10, the gaze duration timer 41 determines $t_{GAZE}$.

The look-direction change unit 43 determines whether a driver's direction of a look changes based upon whether there is a difference between Θ(k) and Θ(k+1). For example, Θ(k) can represent the driver's direction of a look while a visual stimulus is presented at an initial position Q1<x(k),y(k)> while Θ(k+1) can relate to a second position Q2<x(k+1),y(k+1)> of the visual stimulus initial position of a vision stimulus Q1<x(k),y(k)>. This result is outputted to the fatigue decision unit 46.

The look holding time judgment part 44 determines whether a driver's direction of a look stays on a subject for a sufficient amount of time, $T_{MIN}$. It has been determined that a fatigued driver might attempt to move his eyes toward a visual stimulus but be unable to hold his gaze on the visual stimulus for a minimal amount of time sufficient to comprehend the visual stimulus, due to his fatigue. If $t_{GAZE}$ does not meet or exceed $T_{MIN}$, then this may indicate driver fatigue. This result is outputted to the fatigue decision unit 46.

When a visual stimulus is moved from a first position Q1<x(k),y(k)> to a second position Q2 <x(k+1),y(k+1)> by the visual stimulator 20, the locus-change unit 45 determines whether a driver's eyes have followed this movement. For example, no movement has occurred if Q2≈Q1 (if not Q2=Q1). This result is outputted to the fatigue decision unit 46.

Finally, based on the result from one or more of the look-direction-change unit 43, the thresholding unit 44 and the locus-change unit 45, the fatigue decision unit 46 concludes whether the driver is fatigued. Thus, a more accurate assessment of a driver's level of fatigue can be obtained based on locus-change, look-direction-change and/or $t_{GAZE}$.

That is to say, driver condition determining device 100 can determine that a state (fatigue level) of the driver is not suitable for operation in any of the following three cases. The first case is that the driver's direction of look has not turned to a first position of a vision stimulus Q1. The second case is that duration $t_{GAZE}$ of the driver's direction of look when the visual stimulus is at, e.g., Q1, does not at least equal $T_{MIN}$. The third case is that the driver's look locus does not move in response to movement of the visual stimulus from Q1 to Q2.

Figure 3:
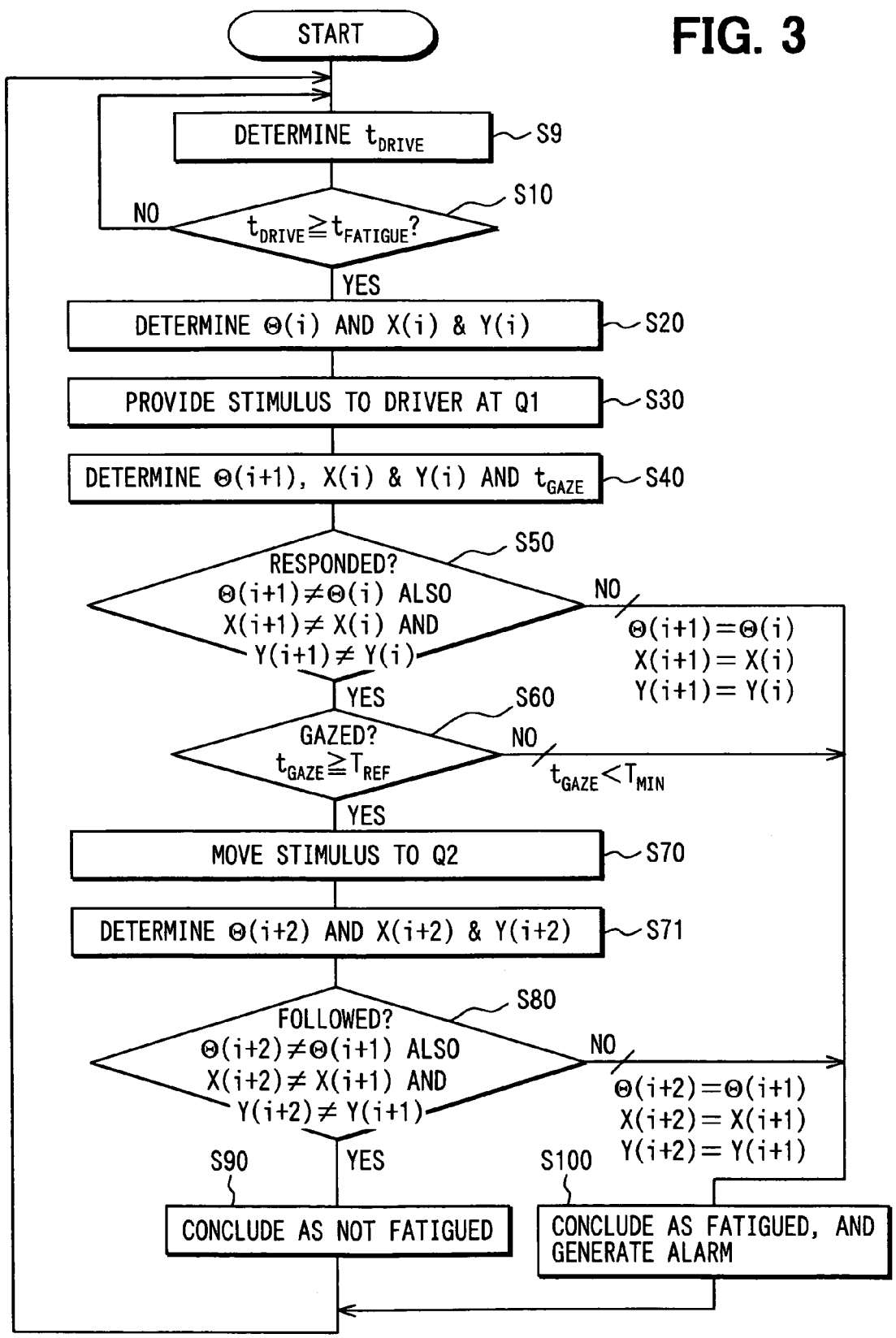
FIG. 3 is a flow chart which shows a method of assessing driver fatigue.

Next, an example method of assessing driver fatigue, e.g., as implemented via driver fatigue assessment device 100, is explained using the flow chart shown in FIG. 3, according to an embodiment of the present invention.

Step 09 determines the time, $t_{DRIVE}$, elapsed since the driver has had to be alert. Step S10 determines whether $t_{DRIVE} \geq t_{FATIGUE}$, i.e., whether fatigue assessment be started At Step S10, if $t_{DRIVE}$ is below the threshold $t_{FATIGUE}$, then flow proceeds back to Step S09. Step S20 determines a first direction ,, (i) and a first two-dimensional position X(i)&Y(i) of a driver's look.

Step S30 provides a visual stimulus to the driver, i.e., inserts the visual stimulus at position Q1 within the driver's field of view, e.g. with the peripheral-vision region thereof. This is depicted in FIG. 5.

Step S40 determines a second look direction ,, (i+1) and position X(i+1)&Y(i+1) of the driver's look. Step S40 also determines a look holding time $t_{GAZE}$, i.e., a time elapsing since the second direction and position were determined.

Step S50 determines whether the driver's eyes have responded to the visual stimulus having been inserted at position Q1. More particularly, Step S50 determines whether "(i+1) "" (i) as well as determines whether X(i+1) "X(i) and Y(i+1) "Y(i). If not, then the driver's eyes have not responded to the visual stimulus, i.e., "(i+1)=" (i), X(i+1)=X(i) and Y(i+1)=Y(i). In that circumstance, i.e., where flow proceeds out the "NO" exit of Step S50, flow will proceed to Step S100 (to be discussed below). But if so, i.e., if flow proceeds out of the "YES" exit of Step S50, then flow proceeds to Step S60.

Step S60 determines if the driver's gaze has lingered long enough upon the visual stimulus. In other words, Step S60 determines if $t_{GAZE} \geq T_{REF}$. If not, i.e., where flow proceeds out the "NO" exit of Step S60, then $t_{GAZE} < T_{REF}$, causing flow to proceed to Step S100 (again, to be discussed below). But if so, then flow proceeds out of the "YES" exit of Step S60 to Step S70.

Figure 6:
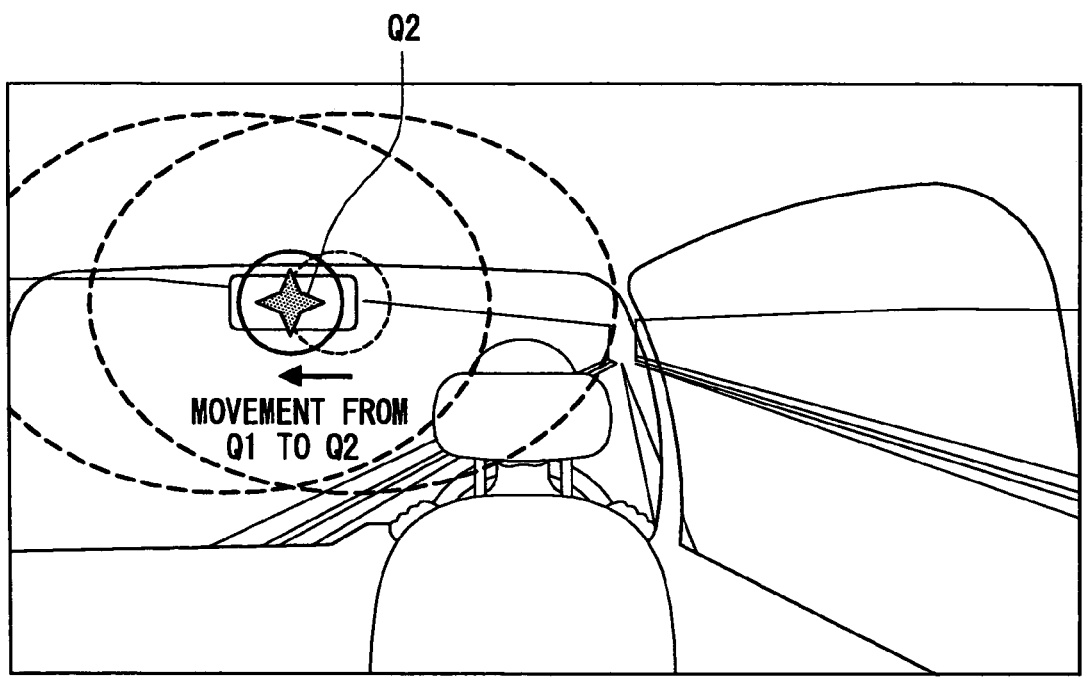
FIG. 6 is a figure showing another position of the visual stimulus, according to an embodiment of the present invention.

Step S70 inserts the visual stimulus at a second position Q2. This is depicted in FIG. 6. Step S71 determines a third direction, (i+2) and position X(i+2)&Y(i+2) of the driver's look.

Steps S80 determines whether the driver's eyes have responded to the visual stimulus having been moved to position Q2 from position Q1. In other words, Step S80 determines whether "(i+2)"" (i+1), and also determines whether X(i+2)"X(i+1) and Y(i+2)" Y(i+1). If not, i.e., if flow proceeds out the "NO" exit of Step 80 such that "(i+2)=" (i+1) and X(i+2)=X(i+1)&Y(i+2)=Y(i+1), then flow proceeds to Step S100. Step S100 concludes that a driver's state is not suitable for operation, e.g., that the driver is exhibiting fatigue. Step S100 also generates an alarm, e.g., the controller 40 causes the alarm device 30 to produce a visual and/or audible output. Flow proceeds from Step S100 and loops back to Step S10.

If flow proceeds out of the "YES" exit of Step S80, then flow proceeds to Step S90, which concludes that the driver's state is suitable for operation, e.g., that the driver is not exhibiting signs of fatigue according to the parameters assessed above.

Alternatively, for example, Steps S50 and/or S60 can be omitted. Also in the alternative, the decision's at Steps S50 and S80 can be based upon only a change in the direction (,, ) of the driver's look or only upon the two-dimensional position (X&Y) of the driver's look.

With some embodiments of the present invention having thus been described, it will be obvious that the same may be varied in many ways. Such variations are not to be regarded as a departure from the spirit and scope of the present invention, and all such modifications are intended to be included within the scope of the present invention.

What is claimed is:

1. A driver fatigue assessment device comprising:
    a look information generator to generate look information regarding at least one of a driver's direction of a look and a locus at which a driver is looking;
    a visual stimulator to provide a visual stimulus within a driver's field of view at a first position and then at a second position; and
    a controller, the controller including:
        a change determination unit to determine whether the look information has changed in response to the change in the visual stimulus position; and
        a fatigue decision unit to assess driver fatigue based upon an output of the change determination unit, wherein the controller is operable to initiate driver fatigue analysis if an elapsed amount of time $t_{DRIVE}$ during which the driver has had to be alert equals a threshold amount of time $T_{FATIGUE}$ associated with the onset of fatigue.

2. The driver fatigue assessment device according to claim 1, wherein:
    the look information generator is further operable to output a first set of look information when the visual stimulus is at the first position and a second set of look information when the visual stimulus is at the second position;
    the change determination unit is further operable to determine whether the first and second sets of look information are different and output a difference indication; and
    the fatigue decision unit is further operable to assess driver fatigue based the difference indication.

3. The driver fatigue assessment device according to claim 1, further comprising:
    a gaze duration timer to measure an elapsed time $t_{GAZE}$ of the driver's gaze; and
    a thresholding unit to determine whether $t_{GAZE}$ at least equals a minimum reference time $T_{REF}$;
    wherein the fatigue decision unit is further operable to assess fatigue based upon an output of the thresholding unit.

4. The driver fatigue assessment device according to claim 1, wherein the first and second positions of the visual stimulus are provided in a peripheral-vision region of the driver's field of view, respectively.

5. The driver fatigue assessment device according to claim 1, further comprising:
    an alarm operable according to an output of the fatigue decision unit.

6. A driver fatigue assessment method comprising:
    detecting a look direction of a driver;
    detecting a look locus at which the driver is looking based upon on the look direction;
    providing a visual stimulus at a first position within the peripheral vision region of the driver;
    moving the visual stimulus to a second position within the peripheral vision region of the driver;
    determining whether the look locus followed the movement of the visual stimulus from the first to the second position;
    assessing a level of fatigue of the driver based upon whether a change in the look locus has been determined; and
    initiating driver fatigue analysis if an elapsed amount of time $t_{DRIVE}$ during which the driver has had to be alert equals a threshold amount of time $T_{FATIGUE}$ associated with the onset of fatigue.

7. The driver fatigue assessment device according to claim 1, wherein the look information generator includes at least one of:
    a direction detector to detect a driver's direction of a look; and
    a look locus determination unit to determine a locus at which a driver is looking.

8. A method of assessing driver fatigue, the method comprising:
    providing a visual stimulus at a first position in a driver's field of view;
    determining at least one of a first direction of a driver's look and a first position at which the driver is looking;
    providing a visual stimulus at a second position in a driver's field of view; and
    determining at least one of a second direction of a driver's look and a second position at which the driver is looking, respectively;
    determining whether the driver's eyes have responded to the change in position of the visual stimulus; and
    initiating driver fatigue analysis if an elapsed amount of time $t_{DRIVE}$ during which the driver has had to be alert equals a threshold amount of time $T_{FATIGUE}$ associated with the onset of fatigue.

9. The method of claim 8, further comprising:
    concluding the driver is fatigued if the driver's eyes have not responded to the change in position of the visual stimulus.

10. The method of claim 8, further comprising:
    generating an alarm if the driver's eyes have not responded to the change in position of the visual stimulus.

11. The method claim 8, further comprising:
    determining an amount of time $t_{GAZE}$ elapsed since the first direction or first position was determined;
    determining if $t_{GAZE} \geq T_{REF}$, where $T_{MIN}$ is a reference minimum amount of time; and
    concluding the driver is fatigued if $t_{GAZE} < T_{MIN}$.

12. The method of claim 11, further comprising:
    generating an alarm if $t_{GAZE} < T_{MIN}$.

13. An apparatus for assessing driver fatigue, the apparatus comprising:
    means for providing a visual stimulus at a first position in a driver's field of view;
    means for determining at least one of a first direction of a driver's look and a first position at which the driver is looking;
    means for providing a visual stimulus at a second position in a driver's field of view; and
    means for determining at least one of a second direction of a driver's look and a second position at which the driver is looking, respectively;
    means for determining whether the driver's eyes have responded to the change in position of the visual stimulus; and
    means for initiating driver fatigue analysis if an elapsed amount of time $t_{DRIVE}$ during which the driver has had to be alert equals a threshold amount of time $T_{FATIGUE}$ associated with the onset of fatigue.

14. A machine-readable medium comprising instructions, execution of which by a machine facilitates assessing driver fatigue, the machine-readable instructions including:

a driver fatigue analysis initiating code segment to initiate driver fatigue analysis if an elapsed amount of time $t_{DRIVE}$ during which the driver has had to be alert equals a threshold amount of time $T_{FATIGUE}$ associated with the onset of fatigue;

a first stimulator code segment to provide a visual stimulus at a first position in a driver's field of view;

a first direction determination code segment to determine at least one of a first direction of a driver's look and a first position at which the driver is looking;

a second stimulator code segment to provide a visual stimulus at a second position in a driver's field of view; and a second direction code segment to determine at least one of a second direction of a driver's look and a second position at which the driver is looking, respectively; and a decision code segment to determine whether the driver's eyes have responded to the change in position of the visual stimulus.

15. The machine-readable instructions of claim 14, wherein execution of the decision code segment further causes the machine to do the following: conclude the driver is fatigued if the driver's eyes have not responded to the change in position of the visual stimulus.

16. The machine-readable instructions of claim 14, further comprising:

a timer segment to measure an amount of time $t_{GAZE}$ elapsed since the first direction or first position was determined; and a thresholding segment to determine if $t_{GAZE} \geq T_{REF}$, where $T_{MIN}$ is a reference minimum amount of time;

wherein execution of the decision segment further causes the machine to conclude the driver is fatigued if $t_{GAZE} < T_{MIN}$.

17. The machine-readable instructions of claim 16, wherein execution of the decision segment further causes the machine to generate an alarm if $t_{GAZE} < T_{MIN}$.

18. A driver fatigue assessment device comprising;

a look information generator to generate look information regarding at least one of a driver's direction of a look and a locus at which a driver is looking;

a visual stimulator to provide a visual stimulus within a driver's field of view; and a controller, the controller including:

a gaze duration determination unit to determine how long the driver gazes at the visual stimulus and to output a time $t_{GAZE}$ indicative thereof;

a thresholding unit to determine whether $t_{GAZE}$ at least equals a minimum reference time $T_{REF}$; and a fatigue decision unit to assess driver fatigue based upon an output of the thresholding unit, wherein the controller is operable to initiate driver fatigue analysis if an elapsed amount of time $t_{DRIVE}$ during which the driver has had to be alert equals a threshold amount of time $T_{FATIGUE}$ associated with the onset of fatigue.

* * * * *